United States Patent
Duong et al.

(10) Patent No.: US 7,621,890 B2
(45) Date of Patent: Nov. 24, 2009

(54) HEAT EXCHANGE CATHETER WITH MULTI-LUMEN TUBE HAVING A FLUID RETURN PASSAGEWAY

(75) Inventors: Thach Duong, Tustin, CA (US); Jay J. Eum, Irvine, CA (US); Jenny C. Liu, Irvine, CA (US)

(73) Assignee: Endocare, Inc., Irvine, CA (US)

( * ) Notice: Subject to any disclaimer, the term of this patent is extended or adjusted under 35 U.S.C. 154(b) by 243 days.

(21) Appl. No.: 11/417,407

(22) Filed: May 4, 2006

(65) Prior Publication Data

US 2006/0282039 A1 Dec. 14, 2006

Related U.S. Application Data

(63) Continuation-in-part of application No. 11/148,454, filed on Jun. 9, 2005.

(51) Int. Cl.
*A61F 7/12* (2006.01)
(52) U.S. Cl. .......................... 604/113; 604/514
(58) Field of Classification Search .............. 604/27, 604/28, 500, 506, 514, 515, 517, 96.01, 101.01, 604/101.02, 113, 114, 264; 607/96, 104, 607/105
See application file for complete search history.

(56) References Cited

U.S. PATENT DOCUMENTS

| | | |
|---|---|---|
| 1,011,606 A | 12/1911 | Fulton |
| 3,087,493 A | 4/1963 | Schossow |
| 4,244,377 A | 1/1981 | Grams |
| 4,813,429 A | 3/1989 | Eshel |
| 4,820,349 A | 4/1989 | Saab |
| 4,823,812 A | 4/1989 | Eshel |
| 5,246,421 A | 9/1993 | Saab |
| 5,248,312 A | 9/1993 | Langberg |
| 5,249,585 A | 10/1993 | Turner |

(Continued)

FOREIGN PATENT DOCUMENTS

WO WO2004/098673 A2 11/2004

OTHER PUBLICATIONS

Onik, Ultrasound-Guided Cryosurgery, Scientific American AT 62 (Jan.1996).

(Continued)

*Primary Examiner*—Kevin C Sirmons
*Assistant Examiner*—Bhisma Mehta
(74) *Attorney, Agent, or Firm*—Lawrence N. Ginsberg

(57) ABSTRACT

The catheter includes a multi-lumen tube having an outflow portion and an accessory portion. The accessory portion is integrally formed within an interior volume of the outflow portion. The accessory portion has a cross-section smaller than the outflow portion. The outflow portion is offset from the accessory portion such that they are integrally joined. The space between these portions defines a fluid return passageway and the space within the accessory portion defines an accessory passageway. A flexible outer sleeve cooperates with the multi-lumen tube to form a fluid inlet passageway. During operation, an inlet flow of warming fluid flows through the fluid inlet passageway formed between the outer sleeve and the multi-lumen tube. The flow continues around a distal end of the outflow portion of the multi-lumen tube, thus becoming an outlet flow of the warming fluid which is directed through the fluid return passageway.

18 Claims, 4 Drawing Sheets

U.S. PATENT DOCUMENTS

| | | | |
|---|---|---|---|
| 5,257,977 A | 11/1993 | Eshel | |
| 5,264,260 A | 11/1993 | Saab | |
| 5,342,301 A | 8/1994 | Saab | |
| 5,358,486 A | 10/1994 | Saab | |
| 5,411,477 A | 5/1995 | Saab | |
| 5,437,673 A * | 8/1995 | Baust et al. | 606/23 |
| 5,456,680 A | 10/1995 | Taylor | |
| 5,460,628 A | 10/1995 | Neuwirth | |
| 5,480,417 A | 1/1996 | Hascoet | |
| 5,499,973 A | 3/1996 | Saab | |
| 5,501,227 A | 3/1996 | Yock | |
| 5,549,559 A | 8/1996 | Eshel | |
| 5,569,195 A | 10/1996 | Saab | |
| 5,624,392 A | 4/1997 | Saab | |
| 5,755,690 A | 5/1998 | Saab | |
| 5,772,659 A | 6/1998 | Becker | |
| 5,827,269 A | 10/1998 | Saadat | |
| 5,843,144 A | 12/1998 | Rudie | |
| 5,902,268 A | 5/1999 | Saab | |
| 6,004,289 A | 12/1999 | Saab | |
| 6,017,361 A | 1/2000 | Mikus | |
| 6,033,399 A | 3/2000 | Gines | |
| 6,067,475 A | 5/2000 | Graves | |
| 6,139,571 A * | 10/2000 | Fuller et al. | 607/105 |
| 6,264,679 B1 | 7/2001 | Keller | |
| 6,414,281 B1 | 7/2002 | Long | |
| 6,419,690 B1 | 7/2002 | Mikus | |
| 6,440,158 B1 | 8/2002 | Saab | |
| 6,623,516 B2 * | 9/2003 | Saab | 607/106 |
| 6,702,840 B2 | 3/2004 | Keller | |
| 6,767,346 B2 | 7/2004 | Damasco | |
| 6,905,494 B2 * | 6/2005 | Yon et al. | 606/24 |
| 6,905,510 B2 | 6/2005 | Saab | |
| 6,966,889 B2 | 11/2005 | Saab | |
| 2002/0177804 A1 | 11/2002 | Saab | |
| 2003/0004456 A1 | 1/2003 | Saab | |
| 2003/0028212 A1 | 2/2003 | Saab | |
| 2003/0055415 A1 | 3/2003 | Yu | |
| 2004/0167593 A1 | 8/2004 | Keller | |
| 2005/0113893 A1 | 5/2005 | Saab | |

OTHER PUBLICATIONS

Onik, Cohen, et al. Transrectal Ultrasound-Guided Percutaneous Radical Cryosurgical Ablation of the Prostate, 72 Cancer 1291 (1993).

Wong, et al. Cryosurgery as a Treatment for Prostate Carcinoma, 79 Cancer 963 (Mar. 1997).

* cited by examiner

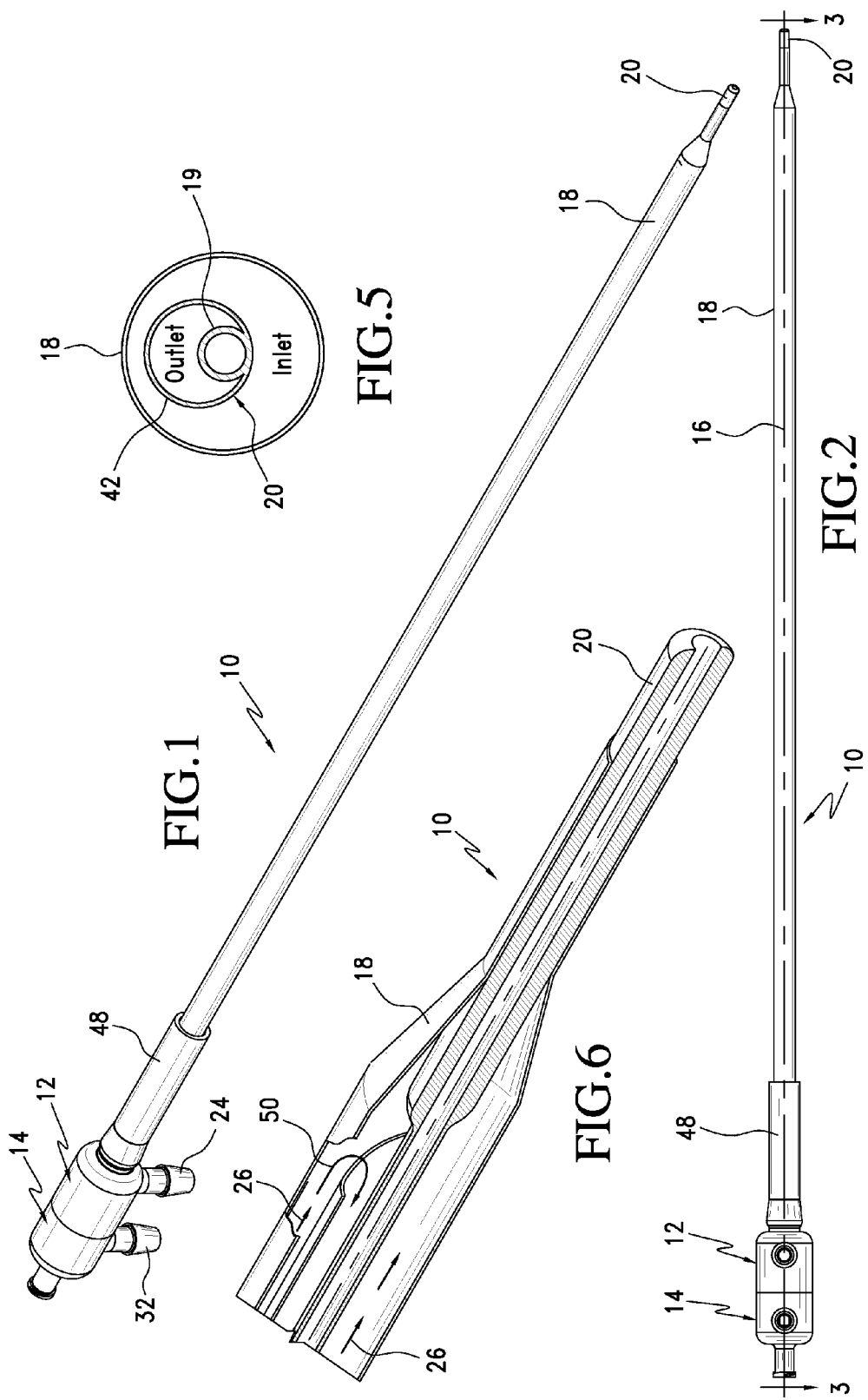

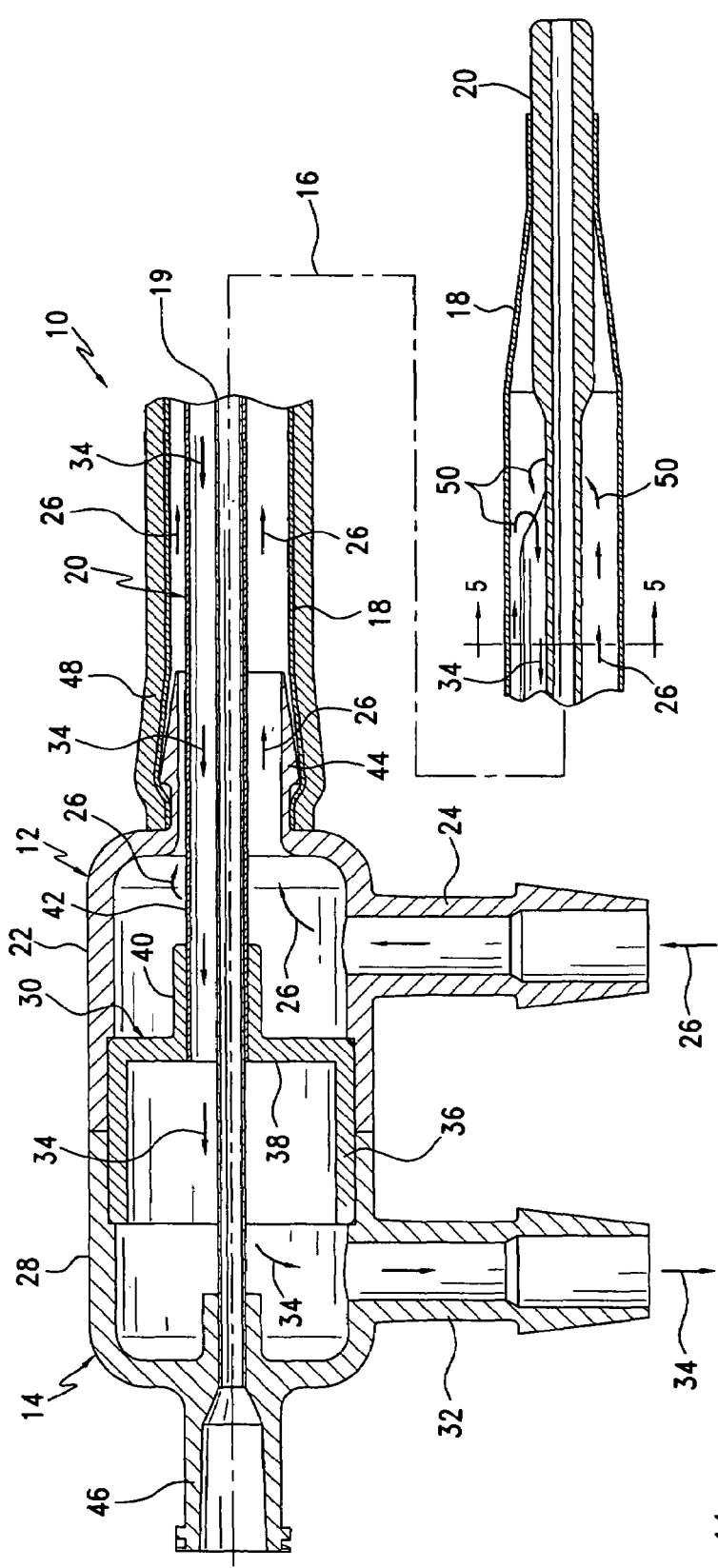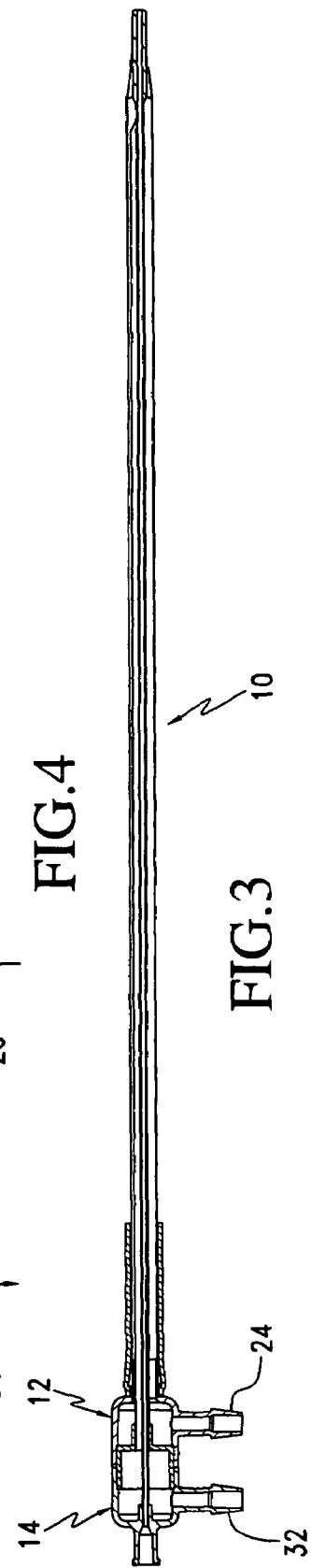
FIG. 4
FIG. 3

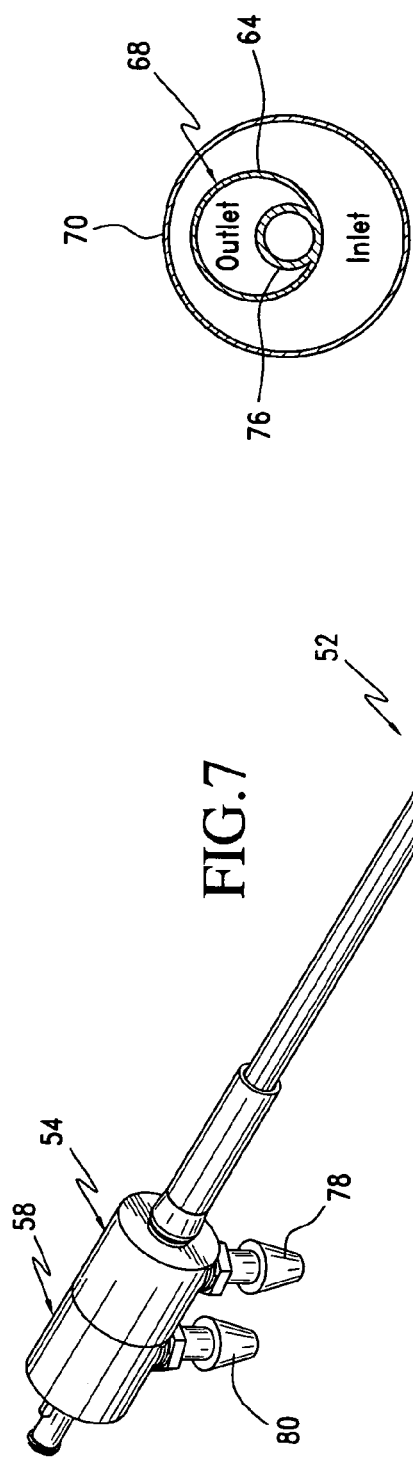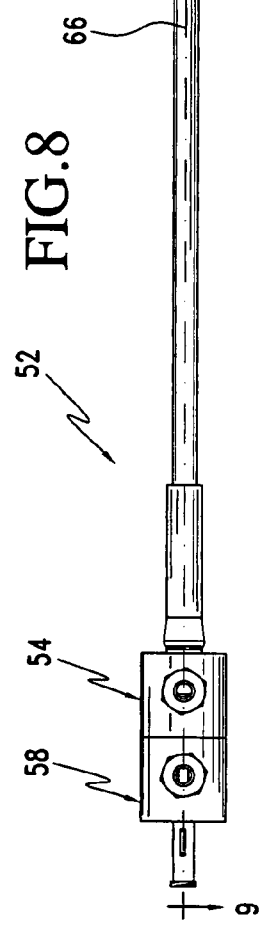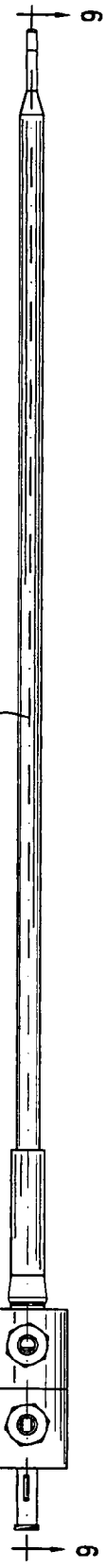

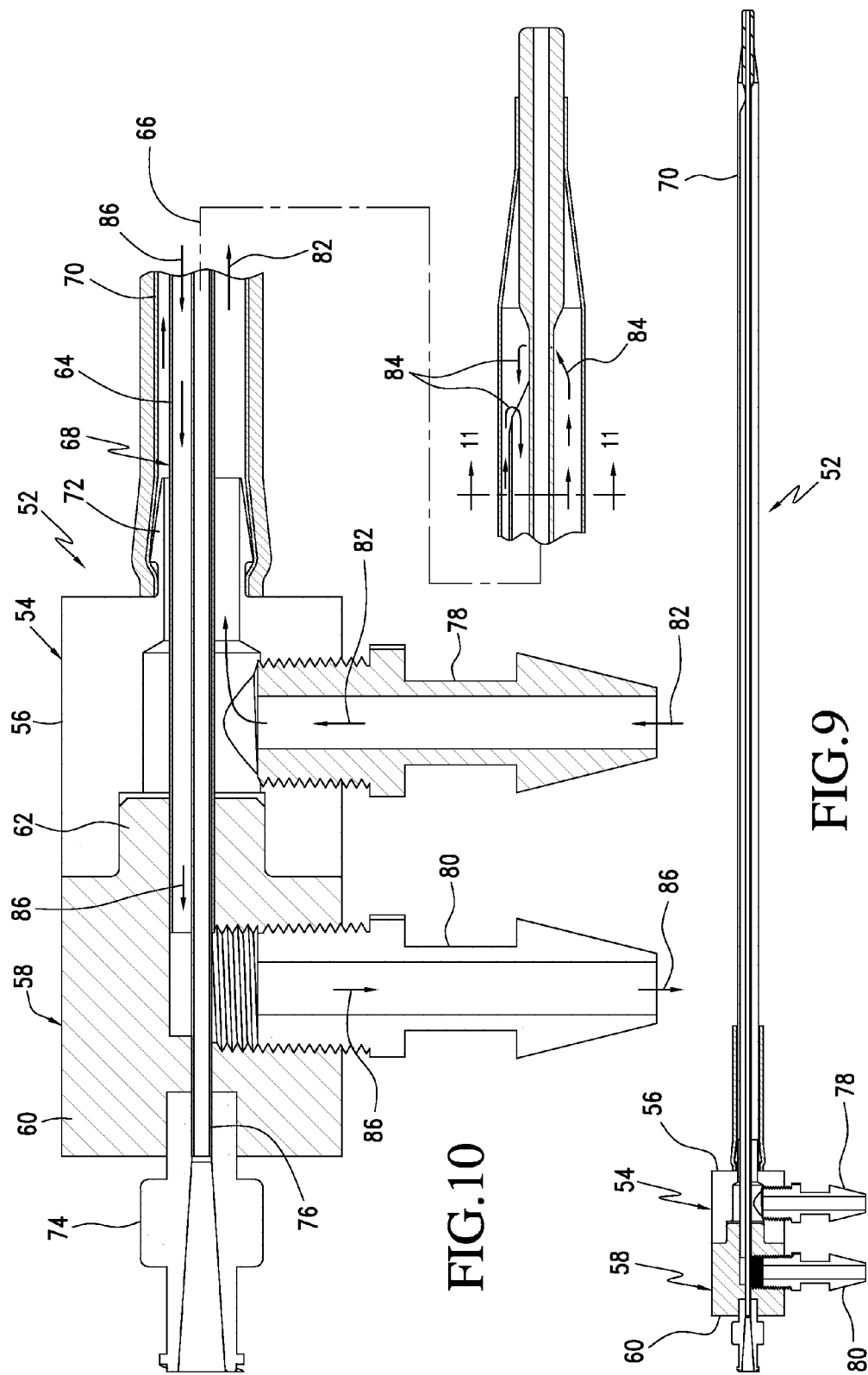

HEAT EXCHANGE CATHETER WITH MULTI-LUMEN TUBE HAVING A FLUID RETURN PASSAGEWAY

CROSS REFERENCE TO RELATED APPLICATIONS

This is a continuation-in-part of U.S. Ser. No. 11/148,454, entitled "Heat Exchange Catheter and Method of Use", filed Jun. 9, 2005.

BACKGROUND OF THE INVENTION

1. Field of the Invention

The present invention relates to urological warming and cooling devices and more particularly to a warming catheter and method of warming the urethra of a patient during ablative surgery. The apparatus is particularly useful in cryosurgery to prevent damage to tissues surrounding a surgical site from the extremely cold temperatures employed therein. The apparatus is especially useful during transperineal cryoablation of the prostate gland in human males to maintain the temperature of the urethral tissues and thereby prevent urethral sloughing. The apparatus may also have utility where it is desired to lower the temperature of surrounding tissues, such as during laser ablation.

2. Description of the Related Art

Cryosurgical probes are used to treat a variety of diseases. The cryosurgical probes quickly freeze diseased body tissue, causing the tissue to die after which it will be absorbed by the body, expelled by the body or sloughed off. Cryothermal treatment is currently used to treat prostate cancer and benign prostate disease, breast tumors and breast cancer, liver tumors and liver cancer, glaucoma and other eye diseases. Cryosurgery is also proposed for the treatment of a number of other diseases.

The use of cryosurgical probes for cryoablation of the prostate is described in, for example, Onik, *Ultrasound-Guided Cryosurgery*, Scientific American at 62 (January 1996). Cryosurgical probe systems are manufactured by present assignee, Endocare, Inc. of Irvine, Calif. In cryosurgical ablation procedures generally several cryosurgical probes are inserted through the skin in the perineal area (between the scrotum and the anus), which provides the easiest access to the prostate. The probes are pushed into the prostate gland through previously placed cannulas. Placement of the probes within the prostate gland is typically visualized with an ultrasound imaging probe placed in the rectum. The probes are quickly cooled to temperatures typically below −120° C. The prostate tissue is killed by the freezing, and any tumor or cancer within the prostate is also killed. The body absorbs some of the dead tissue over a period of several weeks. However, other necrosed tissue may slough off and pass through the urethra, often causing undesirable blockage. Thus, it is often desirable to avoid cryoinjury to the urethra during cryoablation of the prostate. This may be done by placing a warming catheter in the urethra and continuously flushing the catheter with warm fluid to keep the urethra from freezing.

Devices for warming the urethra have been available for quite some time. In 1911, U.S. Pat. No. 1,011,606 issued for an "Appliance For Subjecting Portions Of The Human System To Heat Or Cold." This device was a coaxial dual lumen catheter intended for the application of therapeutic cooling or heating to the urethra and bladder. Devices for warming other body parts have also been proposed, such as U.S. Pat. No. 4,244,377, issued Jan. 13, 1981 to Grams entitled "Ear Probe For Use In Closed-Loop Caloric Irrigation", which shows a coaxial dual lumen cannula intended for the application of therapeutic heating inside the ear.

U.S. Pat. No. 5,437,673, issued on Aug. 1, 1995 to Baust, et al., entitled "Closed Circulation Tissue Warming Apparatus and Method of Using the Same in Prostate Surgery" illustrates use of a urethral warming catheter which is used to protect the urethra from cryothermal damage during cryosurgical treatment of the prostate for benign prostate hyperplasia. The Baust patent discloses a coaxial three lumen catheter in which warm saline passes through an outside lumen and is returned through a coaxial second lumen. A third lumen is a urinary drainage lumen centrally disposed within the other two lumens. The catheter is used to heat the urethra while the prostate is being frozen with cryosurgical probes.

A very similar device to that disclosed in U.S. Pat. No. 5,437,673 is disclosed in U.S. Pat. No. 5,624,392, issued on Apr. 29, 1997 to Saab, entitled "Heat Transfer Catheter and Methods of Making and Using Same." In the Saab '392 device there is a co-axial relationship between the lumens. It is required that inlet flow be directed through the innermost lumen to the end of the end of that lumen and then returned through the outermost lumen. Saab uses a very flexible inner sleeve which would collapse if the direction of this flow was reversed. The devices would collapse if the flow were reversed.

Present applicants are co-inventors of U.S. Ser. No. 11/148,454, entitled Heat Exchange Catheter and Method of Use", filed Jun. 9, 2005. In the '454 device an inlet flow of heat exchange fluid flows from an inflow housing inlet section, and through an inflow housing main section. It then flows through an inlet fluid passageway formed between an inner balloon and a discharge tube. The flow continues around a distal end of the inner balloon, thus becoming an outlet flow of the heat exchange fluid which is directed through an outlet fluid passageway formed between the inner balloon and an outer balloon, then through an outflow housing main section and finally discharged through an outflow housing outlet section. The inner balloon is in a position offset from the central axis of the catheter.

U.S. Pat. No. 5,257,977, issued on Nov. 2, 1993 to Eshel, entitled "Technique for Localized Thermal Treatment of Mammals," shows a catheter that delivers heated saline flow to provide therapeutic hyperthermia treatment of the prostate. Like the Baust patent, Eshel shows a three lumen catheter with a centrally located urinary drainage lumen.

Still other devices have been described for importing fluid into the body and allowing a means for removing fluid from the body. One such device is described in U.S. Pat. No. 3,087,493, issued Apr. 27, 1960 to Schossow, entitled "Endotracheal Tube". Schossow describes a device employed to intubate the human trachea. The device is connected with ducts and/or tubes outside the patient for the purpose of, for example, drawing off from the patient's respiratory tract undesirable liquids and/or introducing beneficial liquids into the trachea. The device comprises an outer tube, which fits inside the patient's trachea, and a two layered inner tube. The lumen of the inner tube is open to be connected with devices or ducts through which suction may be applied or fluids injected into the trachea. The distal portion of the inner tube is vented with ports or openings that create a "sprinkler" effect inside the tube.

During cryoablation, the prostate tissue is killed by freezing temperatures in the cryogenic temperature range, typically −120° C. and below. The hot fluid used for the warming catheter is supplied at about 30° C. to 50° C. Warm fluid is pumped through the urethral warming catheter, such as the catheter described in Baust et al. Using this catheter, as the warm fluid travels the length of the urethral catheter disposed within the cryosurgically-cooled urethra, it is cooled by the surrounding freezing tissue. By the time the hot water has traveled from the bladder neck sphincter to the external sphincter, it has been significantly cooled by the surrounding frozen prostate. As a result, the urethral tissue near the bladder neck sphincter (near the hot water outlet) is heated more than the urethral tissue near the external sphincter, creating a strong thermal gradient in the prostatic urethra and an uneven heating effect. By the time the hot water reaches the external sphincter, it may have lost so much heat to the upper region of the urethra that it is not warm enough to protect the external sphincter from freezing. In order for the tissue at the bladder neck sphincter to be adequately warmed, hotter water must be pumped in, risking urethral damage due to scalded tissue, or more water must be pumped at higher rates and pressures, increasing the material requirements of the hot water supply system and the warming catheter.

U.S. Pat. No. 6,017,361, issued to Mikus et al, entitled "Urethral Warming Catheter," discloses an improved method and means for maintaining the temperature of urethral tissues during cryoablation of the prostate gland and thereby eliminates or reduces the sloughing of dead cells into the urethra. Diffuser holes or ports, much like a "sprinkler," are drilled into the inner tube of the warming catheter. The holes create an advantage over the prior art of achieving improved uniformity of fluid flow and temperature, utilizing a lower initial temperature and resulting in a more even application of thermal treatment to the urethral tissues. The apparatus may find additional utility in other areas of surgery where thermal treatment or maintenance of tissues is required with or without the capability of drainage.

SUMMARY OF THE INVENTION

In a broad aspect the present invention is a heat exchange catheter that includes an inflow housing assembly for receiving an inlet flow of warming fluid. An outflow housing assembly receives an outlet flow of warming fluid. A multi-lumen tube includes an outflow portion and an accessory portion. The accessory portion is integrally formed within an interior volume of the outflow portion. The accessory portion has a cross-section smaller than the outflow portion. The outflow portion is offset from the accessory portion such that the outflow portion and the accessory portion are integrally joined. The space between the outflow portion and the accessory portion defines a fluid return passageway and the space within the accessory portion defines an accessory passageway. A flexible outer sleeve cooperates with the multi-lumen tube positioned therein to form a fluid inlet passageway. Flow separation means separates the inlet flow of warming fluid from the outlet flow of warming fluid. During operation, the inlet flow of warming fluid flows from the inflow housing assembly, then through the fluid inlet passageway formed between the outer sleeve and the multi-lumen tube. The flow continues around a distal end of the outflow portion of the multi-lumen tube, thus becoming the outlet flow of the warming fluid which is directed through the fluid return passageway, then through the outflow housing assembly.

The heat exchange catheter is particularly useful as a warming catheter for prostatic cryosurgical procedures where cryosurgical probes are used and it is desired to maintain the temperature of the urethral tissues to prevent urethral sloughing.

Utilization of a multi-lumen tube has several advantages over the '673 device discussed above. Since the inlet flow is on the outside of the heat exchange catheter heat transfer is optimized. The cost is minimized because there are fewer parts to be manufactured. Furthermore, more standard processes may be used during manufacturing.

Offset positioning of the outflow portion of the multi-lumen tube relative to the outer sleeve, in contrast to any coaxial relationship of these elements and the accessory portion of the multi-lumen tube has certain advantages. An offset relationship enhances the fluid dynamic properties of the catheter. It provides an increased turbulence, which, in turn, maximizes the heat exchange efficiency.

Furthermore, this offset positioning provides the ability to have an accessory portion of the multi-lumen tube of minimal thickness and thus enhanced flexibility, which is important, for example, for application in the urethra in which the catheter must be able to bend around the pubic bone when inserted through the urethra.

BRIEF DESCRIPTION OF THE DRAWINGS

FIG. 1 is a perspective view of a first embodiment of the heat exchange catheter of the present invention.

FIG. 2 is a bottom plan view of the embodiment of FIG. 1.

FIG. 3 is a cross-sectional view taken along line 3-3 of FIG. 2.

FIG. 4 is an enlarged cross-sectional view of the invention.

FIG. 5 is a sectional view taken along lines 5-5 of FIG. 4.

FIG. 6 is a perspective view of the distal portion of the heat exchange catheter.

FIG. 7 is a perspective view of a second embodiment of the heat exchange catheter of the present invention.

FIG. 8 is a bottom plan view of the embodiment of FIG. 7.

FIG. 9 is a cross-sectional view taken along line 9-9 of FIG. 8.

FIG. 10 is an enlarged cross-sectional view of the second embodiment of the invention.

FIG. 11 is a sectional view taken along lines 11-11 of FIG. 10.

DETAILED DESCRIPTION OF THE PREFERRED EMBODIMENTS

Referring now to the drawings and the characters of reference marked thereon, FIGS. 1-6 illustrate a first embodiment of the heat exchange catheter of the present invention, designated generally as 10. The catheter 10 includes an inflow housing assembly, designated generally as 12 and an outflow housing assembly, designated generally as 14. The generally cylindrical housing assemblies 12, 14 are coupled to each other and are serially positioned along a common central axis 16. A flexible outer sleeve 18 projects from the distal end of the inflow housing assembly 12. An accessory portion 19 of a multi-lumen tube, designated generally as 20, is also positioned along the central axis 16 and extends beyond the end of the outer sleeve 18.

As best seen with reference to FIG. 4, the inflow housing assembly 12 includes an inflow housing main section 22 and an inflow housing inlet section 24 coupled to the inflow housing main section for providing an inlet flow of warming fluid to the inflow housing main section. The inflow housing main section 22 and the inflow housing inlet section 24 have respective openings therein for providing for the inlet flow, designated by arrows 26. In the embodiment shown, the inflow housing main section 22 and the inflow housing inlet section 24 together comprise an integral, molded plastic part.

The outflow housing assembly 14 includes an outflow housing main section 28, which is along the central axis 16 of the inflow housing main section 22. The outflow housing main section 28 is coupled to the inflow housing main section 22 via a divider element (i.e. flow separator means), designated generally as 30. An outflow housing outlet section 32 is coupled to the outflow housing main section 28 for receiving an outlet flow of warming fluid from the outflow housing main section 28, the outlet flow, designated by arrows 34. The outflow housing main section 28 and the outflow housing outlet section 32 have respective openings for the inlet flow 26 and the outlet flow 34.

The divider element 30 includes a proximal axially oriented portion 36 secured to a proximal end of the inflow housing main section 22 and to a distal end of the outflow housing main section 28. A radially inwardly extending portion 38 depends from a distal end of the proximal axially oriented portion 36. The radially inward extending portion 38 is radially off center from the central axis 16. A distal axially oriented portion 40 depends from the radially inwardly extending portion 38. The distal axially oriented portion 40 is secured to a proximal end of an outflow portion 42 of the multi-lumen tube 20. Thus, the multi-lumen tube 20 central axis (which is also the central axis of the outflow portion 42) is positioned offset from the central axis 16. The inflow housing main section 22 includes an axial extension 44. The outer sleeve 18 is secured between the outer surface of the axial extension 44 and a strain relief element 48. Although FIG. 4 illustrates the outflow portion 42 of the multi-lumen tube 20 being secured to the inner surface of the distal axially oriented portion 40 it may be secured in other locations such as the outer surface of the distal axially oriented portion 40.

A LUER fitting 46 extends rearwardly from a proximal end of the outflow housing main section 28 for providing access to the accessory portion 19. The discharge tube 20 may provide access for the discharge of bladder fluid or may, for example, provide access for a guide wire or endoscope.

The outer sleeve 18 is preferably made from a flexible, relatively non-stretchable, polyester film such as polyethylene terephthalate (PET), having a fixed diameter upon introduction of fluid therein. Preferably, this diameter is about 22 French, which corresponds to the average diameter of the urethra in adult male humans. (This is an outside diameter of about 0.288 inches.) It may have an inside diameter of about 0.285 inches. The length of the outer sleeve 18 may be on the order of, for example, from about 12 inches to about 24 inches.

As can be seen in FIG. 5, the accessory portion 19 of the multi-lumen tube 20 is integrally formed within an interior volume of the outflow portion 42. Both portions 19, 14 preferably have substantially circular cross-sections. The accessory portion 19 has a cross-section smaller than the outflow portion 42. The outflow portion 42 is offset from the accessory portion 19 such that the outflow portion 42 and the accessory portion 19 are integrally joined at a common wall. The space between the outflow portion 42 and the accessory portion 19 defines a fluid return passageway and the space within the accessory portion defines an accessory passageway.

The multi-lumen tube 20 may be formed of, for example, a suitable plastic such as polyethylene. The outflow portion 42 may have an outside diameter of about 0.162 inches and an inside diameter of about 0.148 inches. Therefore, the wall thickness of the outflow portion 42 is about 0.007 inches. Generally, the outflow portion may have a wall thickness in a range of about 0.005-0.009 inches. The outflow portion 42 is required to be sufficiently rigid so that the inlet flow does not collapse the outflow portion 42. The accessory portion may, for example, have an outside diameter of about 0.079 inches and an inside diameter of about 0.055 inches. Therefore, the wall thickness of the accessory portion 19 may be, for example, about 0.012 inches. Generally, the accessory portion may have a wall thickness in a range of about 0.009-0.017 inches. Thus, the multi-lumen tube 20 is essentially non-collapsible.

As protection against damage due to excessive flexing, a strain relief element 48 in the form of a length of heavier gauge plastic tubing is attached to the inflow housing assembly 12 by telescoping a portion of the tubing over the outer surface of barbed axial extension 44. Strain relief element 48 extends a distance of approximately five centimeters beyond the end of axial extension 44.

In a specific example of operation, to warm a urethra of a patient during cryosurgical ablative surgery, ablative devices are inserted into the prostate region of a patient. The heat exchange catheter 10, operating as a warming catheter, is inserted through the patient's urethra at least to the bladder neck and generally into the bladder. Warming fluid is delivered through the catheter 10 during operation of the ablative surgical devices. The warming fluid is delivered into the bladder. The urethra is warmed by the warming fluid to preserve living tissue thereof.

The ablative devices are preferably cryosurgical probes such as manufactured and marketed by Endocare, Inc., of Irvine, Calif. Generally, six cryosurgical probes are used as well as four temperature probes. Alternatively, other ablative devices may be used, for example, radio frequency electrodes, laser fibers, microwave catheters, or high-intensity focused ultrasound. In such instances the heat exchange fluid is cool so as to prevent the urethra from the heating by the ablative elements.

Although not shown, the inflow housing assembly 12 receives heat exchanges fluid from a pump and warmer, which are, in turn, connected to a reservoir. The warming fluid should be supplied at temperatures sufficient so as to not thermally damage the urethra. Appropriate fluids include sterile water, physiological saline, and the like and should be such fluids as are biocompatible and physiologically benign in the event of inadvertent rupture of the outer sleeve 18.

The warming fluid passes through the inflow housing assembly 12, as shown by arrows 26, and into the inlet fluid passageway formed within the flexible outer sleeve 18. As the flow reaches the distal end of the outer sleeve 18 it is turned, as indicated by arrows 50 (shown in FIGS. 4 and 6), and is directed in the outlet fluid passageway formed between the outflow portion 42 and the accessory portion 19 as indicated by arrows 34. It is then discharged through the outflow housing outlet section 32. Thus, a closed fluid circulation path is provided as the fluid is returned to the reservoir. The counter-current flow of incoming and outgoing fluid allows the warmer incoming fluid in outer sleeve 18 to warm the cooler outgoing fluid in the multi-lumen tube 20. The thermal exchange is even along the length of catheter 10.

The entire apparatus of the catheter 10 may be constructed in larger or smaller sizes as needed depending on the criteria of patient and use. For example, a catheter 10 for use on a child will be smaller than that used on an adult. Similarly, a catheter 10 for use elsewhere in the body may be smaller or larger than that used in the urethra.

Referring now to FIGS. 7-11, another embodiment of the present is illustrated, designated generally as 52. In this instance, the inflow housing assembly 54 includes an inflow housing main section 56 that comprises an inflow block. Similarly, the outflow housing assembly 58 includes an outflow housing main section 60 that comprises an outflow block.

The outflow block has an axial extension 62 having a decreased diameter. A mating surface is formed by the presentation of the axial extension 62 being offset from the central axis 66. An inner radial surface of the axial extension 62 is secured to an outer surface of the outflow portion 64 of the multi-lumen tube 68. The outer sleeve 70 may be secured to an outer surface of an axial extension 72 of the inflow housing main section 56, as shown in FIG. 10. Alternatively, it may be secured to an inner surface of the axial extension 72.

A LUER fitting 74 is secured to and extends from a proximal end of the outflow housing main section 60 for providing access to an accessory portion 76 of the multi-lumen tube 68. In this embodiment, the inflow housing inlet section 78 and outflow housing outlet section 80 are separate pieces from their respective main sections 56, 60. They are threaded into their positions relative to their associated main sections. The flow separation means in this embodiment is the material that forms the blocks 56, 60. Inlet fluid passageways and outlet fluid passageways are provided within these blocks.

This embodiment operates in the same manner as that described above with respect to the first embodiment with inlet flow, designated by arrows 82, passing through the inflow housing assembly 54, around the distal end of the outflow portion 64 as shown by arrows 84. The flow thus becomes an output flow 86 that flows through the outflow housing assembly 58.

Although the examples discussed above refer to the use of a warming fluid it is understood that if the ablative devices are for heating rather than for cooling, the heat exchange fluid would be a cooling fluid.

The heat exchange catheter may find additional utility in other areas of surgery where thermal treatment of maintenance of tissues is required with or without the capability of drainage. For example, an extended length catheter may be used for thermal treatment within the intestinal tract or the esophagus. Shorter versions may find utility in other areas such as nasal passages, otic areas, joints, i.e. arthroscopy, or the like, where adjacent tissues may be undergoing cryogenic or other thermal treatment. Indeed, varied forms of the apparatus and method may be used in virtually any body cavity where tissues are exposed to thermal extremes and damage to adjacent tissues is to be avoided. They may find particular utility anywhere cryogenic probe devices are being used to destroy and/or remove tumerous growths.

The molded embodiment of FIGS. 1-6 has fewer parts than the block embodiment of FIGS. 7-11 and therefore has manufacturing advantages. Molding rather than using machined and standard off the shelf components results in cost advantages. The block embodiment of FIGS. 7-11 has the advantage of obviating up front tooling expenses.

The reservoir used is preferably a removable and disposable plastic container, such as an intravenous bag or a rigid container, which may be prepackaged with a fixed volume of sterile fluid, for example one liter. Clearly, just as larger or smaller catheters may be used in different situations, such larger and smaller catheters will require larger or smaller volumes of fluid. Appropriate fluids include sterile water, physiological saline, and the like and should be such fluids as are biocompatible and physiologically benign in the event of inadvertent rupture of the balloons. To allow for removal and return of the fluid in the closed system, the reservoir includes two fittings for connection of the inflow housing inlet section and outflow housing outlet section. These fittings may be standard piercable IV bag fittings.

A heating block is configured to removably accept and hold reservoir so as to heat the fluid contained therein. Preferably the heating block includes a vertical slot or window, which permits volume indicia on the reservoir to be viewed. The heating block itself may be a simple resistance heating means or an infrared heater or any other suitable heater capable of raising the temperature of the fluid within reservoir to approximately 42 degrees C. Heating the circulation fluid to this level has been found to provide sufficient warmth within the balloons to counter the cold of a cryoprobe and maintain the urethral tissues at about normal body temperature during cryogenic surgery of the prostate. Suitable heater control means allows the operator to select the desired temperature for heater block.

Downstream from the heating block is a pump, which provides motive force to the fluid to maintain a constant and even flow through the system. Once the desired flow rate and temperature are set, automatic control means are activated to maintain these levels. The automatic controls include monitoring sensors for supply temperature, return temperature and flow rate. In addition to the sensors and control means, pump and heater activating switches are included and electrically linked through a control circuit to their respective units as is a low flow alarm.

Thus, while the preferred embodiments of the devices and methods have been described in reference to the environment in which they were developed, they are merely illustrative of the principles of the invention. Other embodiments and configurations may be devised without departing from the spirit of the invention and the scope of the appended claims.

The invention claimed is:

1. A heat exchange catheter for warming the urethra of a patient during ablative surgery, comprising:
    a) an inflow housing assembly for receiving an inlet flow of warming fluid;
    b) an outflow housing assembly for receiving an outlet flow of warming fluid;
    c) a multi-lumen tube comprising an outflow portion and an accessory portion, said accessory portion being integrally formed within an interior volume of said outflow portion, said accessory portion having a cross-section smaller than said outflow portion, said outflow portion having a central axis being offset from a central axis of said accessory portion such that said outflow portion and said accessory portion are integrally joined, wherein the space between said outflow portion and said accessory portion defines a fluid return passageway and the space within said accessory portion defines an accessory passageway;
    d) a flexible outer sleeve cooperating with said multi-lumen tube positioned therein to form a fluid inlet passageway; and,
    e) flow separation means for separating the inlet flow of warming fluid from said outlet flow of warming fluid,
    wherein during operation said inlet flow of warming fluid flows from said inflow housing assembly, then through said fluid inlet passageway formed between said outer sleeve and said multi-lumen tube, the flow continuing around a distal end of said outflow portion of said multi-lumen tube, thus becoming said outlet flow of said warming fluid which is directed through said fluid return passageway, then through said outflow housing assembly.

2. The heat exchange catheter of claim 1, wherein said outflow portion and said accessory portion each have substantially circular cross-sections.

3. The heat exchange catheter of claim 1, wherein said outflow portion and said accessory portion are integrally joined at a common wall.

4. The heat exchange catheter of claim 1, wherein said outflow portion has a wall thickness that is less than the wall thickness of said accessory portion.

5. The heat exchange catheter of claim 1, wherein said outflow portion has a wall thickness in a range of about 0.005-0.009 inches.

6. The heat exchange catheter of claim 1, wherein said accessory portion has a wall thickness in a range of about 0.009-0.017 inches.

7. The heat exchange catheter of claim 1, wherein said multi-lumen tube is formed of polyethylene.

8. The heat exchange catheter of claim 1, wherein:
  a. said inflow housing assembly, comprises:
    i. inflow housing main section having a central axis; and,
    ii. an inflow housing inlet section coupled to said inflow housing main section for providing an inlet flow of warming fluid to said inflow housing main section, said inflow housing main section and said inflow housing inlet section having respective openings therein for providing for said inlet flow; and,
  b. said outflow housing assembly, comprises:
    i. an outflow housing main section having a central axis which is along said central axis of said inflow housing main section, said outflow housing main section being coupled to said inflow housing main section; and,
    ii. an outflow housing outlet section coupled to said outflow housing main section for receiving an outlet flow of warming fluid from said outflow housing main section.

9. The heat exchange catheter of claim 8, wherein said flow separation means comprises a divider element secured to said inflow housing assembly and said outflow housing assembly, said divider element comprising:
  a. a proximal axially oriented portion secured to a proximal end of said inflow housing main section and to a distal end of said outflow housing main section;
  b. a radially inwardly extending portion depending from a distal end of said proximal axially oriented portion, said radially inward extending portion being radially off center from said central axis; and,
  c. a distal axially oriented portion depending from said radially inwardly extending portion, said distal axially oriented portion being secured to a proximal end of said outflow portion of said multi-lumen tube thus positioning said multi-lumen tube in an offset position.

10. The heat exchange catheter of claim 8, wherein said outflow housing assembly further includes a LUER fitting extending from a proximal end of said outflow housing main section for providing access to said accessory portion.

11. The heat exchange catheter of claim 8, wherein said inflow housing main section includes an axial extension, said outer sleeve being secured to said axial extension.

12. The heat exchange catheter of claim 8, further comprising a strain relief element secured about an outer periphery of an axial extension of said inflow housing main section.

13. The heat exchange catheter of claim 8, wherein said inflow housing main section comprises an inflow block and said outflow housing main section comprises an outflow block, said outflow block having an axial extension having a decreased diameter, a mating surface formed by the presentation of said axial extension being offset from a central axis of the outflow housing main section, an inner radial surface of said axial extension being secured to an outer surface of said outflow portion of said multi-lumen tube.

14. The heat exchange catheter of claim 13, wherein said outflow housing assembly further includes a LUER fitting extending from a proximal end of said outflow housing main section for providing access to said accessory portion.

15. The heat exchange catheter of claim 13, wherein said inflow housing main section includes an axial extension, said outer sleeve being secured to said axial extension.

16. The heat exchange catheter of claim 13, further comprising a strain relief element secured about an outer periphery of an axial extension of said inflow housing main section.

17. A method for warming the urethra of a patient during ablative surgery, comprising the steps of:
  a. inserting at least one ablative surgical device into a prostate region of the patient;
  b. inserting a heat exchange catheter through the patient's urethra and at least to the bladder neck, said heat exchange catheter, comprising:
    i. an inflow housing assembly for receiving an inlet flow of warming fluid;
    ii. an outflow housing assembly for receiving an outlet flow of warming fluid;
    iii. a multi-lumen tube comprising an outflow portion and an accessory portion, said accessory portion being integrally formed within an interior volume of said outflow portion, said accessory portion having a cross-section smaller than said outflow portion, said outflow portion having a central axis being offset from a central axis of said accessory portion such that said outflow portion and said accessory portion are integrally joined, wherein the space between said outflow portion and said accessory portion defines a fluid return passageway and the space within said accessory portion defines an accessory passageway;
    iv. a flexible outer sleeve cooperating with said multi-lumen tube positioned therein to form a fluid inlet passageway; and,
    v. flow separation means for separating the inlet flow of warming fluid from said outlet flow of warming fluid; and,
  c. operating said heat exchange catheter to warm an outer surface thereof during operation of said at least one ablative surgical device,
wherein during operation said inlet flow of warming fluid flows from said inflow housing assembly, then through said fluid inlet passageway formed between said outer sleeve and said multi-lumen tube, the flow continuing around a distal end of said outflow portion of said multi-lumen tube, thus becoming said outlet flow of said warming fluid which is directed through said fluid return passageway, then through said outflow housing assembly; and,
wherein said urethra is warmed by said outer surface of said heat exchange catheter to preserve living tissue thereof.

18. The method of claim 17, wherein said step of inserting at least one ablative surgical device into a prostate region of the patient, comprises inserting at least one cryosurgical probe.

* * * * *